United States Patent [19]
Alesi, Jr.

[11] Patent Number: 5,330,964
[45] Date of Patent: Jul. 19, 1994

[54] METHOD OF CONTROLLING VEGETATION

[76] Inventor: Carl A. Alesi, Jr., 1544 Broad Run Rd., Dowingtown, Pa. 19355

[21] Appl. No.: 22,062

[22] Filed: Feb. 24, 1993

[51] Int. Cl.$^5$ .............................................. A01N 59/00
[52] U.S. Cl. .................................... 504/119; 504/116; 504/306; 424/715; 424/717
[58] Field of Search ....................... 504/306, 116, 119; 424/717, 715

[56] References Cited

U.S. PATENT DOCUMENTS

| | | | |
|---|---|---|---|
| 615,444 | 12/1898 | Gammack | 504/120 |
| 696,836 | 4/1902 | McLelland | 504/119 |
| 1,054,796 | 3/1913 | Staow | 504/119 |
| 1,354,043 | 9/1920 | Kramer | 504/116 |
| 1,534,289 | 4/1925 | Teppet | 504/116 |
| 1,694,205 | 12/1928 | Chipman | 504/116 |
| 2,629,655 | 2/1953 | Stark | 504/119 |

FOREIGN PATENT DOCUMENTS 2029701 3/1990 United Kingdom .

*Primary Examiner*—Glennon H. Hollrah
*Assistant Examiner*—Devorah Lambkin
*Attorney, Agent, or Firm*—Howson and Howson

[57] ABSTRACT

A method for controlling the growth of vegetation by applying sodium bicarbonate on and around the unwanted vegetation.

3 Claims, No Drawings

5,330,964

METHOD OF CONTROLLING VEGETATION

FIELD ON THE INVENTION

The present invention relates to an environmentally safe method of controlling vegetation, including but not limited to weeds, moss, poison ivy, clover, grasses and the like. More particularly, the present invention relates to a method of using sodium bicarbonate as a herbicide.

BACKGROUND OF THE INVENTION

There are many known uses of sodium bicarbonate ($NaHCO_3$). For instance, sodium bicarbonate is used in baking as the primary ingredient in baking soda and baking powder which provides a $CO_2$ source for leavening. Sodium bicarbonate is also commonly used as a cleaner and in many medications such as a wash or enema. Industrially, sodium bicarbonate is an intermediate product to many compounds and especially to $Na_2CO_3$ in the Solvay Process. Additionally, sodium bicarbonate can be used to kill household ants.

There are many known herbicides used to control vegetation. Some herbicides are selective, e.g. to control broad leaf weeds growing among grass, while others control a wider range of plant species. Some herbicides act to control vegetation when the active ingredient of the herbicide comes into contact with the leaves of the plant, while others saturate the soil around the plant's roots and are subsequently absorbed by the roots.

A major disadvantage of many of the known herbicides is that they are not only toxic to the unwanted vegetation, but are also hazardous to man, the environment, and wildlife. For instance, the user of a toxic herbicide must be concerned with direct contact of the active ingredient of the herbicide with the skin or eyes, and with vapors emitted by the herbicide being inhaled into the lungs. Also of concern is the longevity of the herbicide residues remaining active in the soil which creates a potential for run off of the toxic herbicides into the ground water. Many of the active ingredients used in herbicides are known carcinogens.

It is known to use arsenic compounds as herbicides. U.S. Pat. No. 615,444 discloses a herbicide using arsenic as the active ingredient. The disadvantage of using arsenic is that it has a high mammalian toxicity and its use in herbicides is extremely hazardous to man, the environment and wildlife. The composition of the '444 patent also contains sodium carbonate but, not as an active ingredient. Rather, it appears to assist in rendering the solution stable. The use of sodium carbonate is also disclosed in U.S. Pat. No. 1,054,796 as a component in a solution for treating infections in trees.

A method disclosed in U.S. Pat. No. 1,534,289 uses sodium chlorate as a herbicide. The '289 patent suggests the use of a herbicide solution in which a small amount of sodium bicarbonate is a component; however, the active ingredient of the solution is sodium chlorate, not the sodium bicarbonate.

OBJECTS OF THE INVENTION

With the foregoing in mind, a primary object of the present invention is to provide an improved method for controlling a wide variety of vegetation which, when used moderately, will have no adverse effect on man, the environment or wildlife.

Another object of the present invention is to provide a method for controlling vegetation which uses as its active ingredient a substance which is not toxic to humans or animals, and is both inexpensive and readily available to the consuming public.

A further object of the present invention is to provide a method for killing vegetation which will result in quick destruction of the existing vegetation and prevent the growth of new vegetation in the treated area for as long as several years without creating the potential for polluting the ground water.

SUMMARY OF THE INVENTION

More specifically, in the method of the present invention the aforementioned objects are accomplished by providing a small but effective quantity of sodium bicarbonate, either in solid or solution form, adjacent an area of vegetation, and applying it directly upon the vegetation to be destroyed and the area where new vegetation is to be prevented.

DESCRIPTION OF THE PREFERRED METHOD

The first step of the preferred method is to supply a quantity of sodium bicarbonate to the area of the unwanted vegetation. Sodium bicarbonate is readily available to the average consumer since the average consumer has many other uses for it, for instance, common household baking powder.

The second step of the preferred method is to sprinkle sodium bicarbonate in solid form as a powder in the area of the unwanted vegetation forming a coating of sodium bicarbonate on the vegetation. Although the thickness of the coating of sodium bicarbonate can vary, it was found that an approximate one-eighth inch coating yields satisfactory results. The coating of sodium bicarbonate can be applied directly on the vegetation or, alternatively, the coating of sodium bicarbonate can be applied on the surface of the soil adjacent to the unwanted vegetation. For best results, the sodium bicarbonate can be applied both on the unwanted vegetation and on the soil around the unwanted vegetation.

Tests have shown that the growth of the unwanted vegetation will begin to diminish within a twenty-four to forty-eight hour period after applying the coating of sodium bicarbonate. The unwanted vegetation will completely die off shortly thereafter.

Growth of new vegetation in the treated area will also be controlled. Tests to date have shown that after an initial one-eighth inch coating of sodium bicarbonate, no new vegetation growth has occurred in the treated area for approximately two years. The control of new vegetation growth is not limited to two years. Tests have yet to be conducted long enough to ascertain the exact period of time in which new growth is controlled. The longevity of growth control is a function of the thickness of the coating of sodium bicarbonate. Therefore, the thickness of the coating applied can be varied to modify the length of time new growth in the treated area is to be controlled. For long periods of controlled new growth, a coating thickness of greater than one-eighth inch can be applied. For short periods of controlled new growth, a coating thickness of less than one-eighth inch can be applied.

An additional step of wetting the unwanted vegetation and adjacent soil with water prior to applying the coating of sodium bicarbonate can be administered. Alternatively, the sodium bicarbonate can be applied to vegetation wet by morning dew or wet by a recent rainfall. Tests have shown that the coating of sodium bicarbonate on wet vegetation and soil tends to take effect on the vegetation quicker than on dry vegetation and soil. While the step of moistening the vegetation and soil enhances the speed with which the control of the growth is effected, an application of sodium bicarbonate on dry vegetation and soil will result in satisfactory growth control.

While the precise theory by which the sodium bicarbonate operates to control vegetation cannot be fully explained, it appears from the practical results of tests performed using the method of the present invention, that a toxic action of some type takes effect on the life-giving constituents of the foliage, stems, stalks and roots of the vegetation treated with sodium bicarbonate.

One alternate embodiment of practicing the method of the invention involves applying the sodium bicarbonate in the form of an aqueous solution. The sodium bicarbonate can be dissolved in water, or any compatible solvent, and sprayed onto the unwanted vegetation and surrounding ground surface. The solution can be of any desired concentration, but for purposes of example, a solution of one part water and one part sodium bicarbonate, by volume, will provide satisfactory results. The solution should be sprayed to an extent sufficient to soak the vegetation, or the surrounding soil, or both. The extent to which the vegetation and surrounding soil are soaked, as well as the concentration of the solution, will affect both the speed at which the existing vegetation is controlled and the longevity of controlling new vegetation growth.

While a preferred method of practicing the invention has been described, various modifications, alterations and changes may be made without departing from the spirit and scope of the invention as defined in the appended claims.

I claim:

1. An environmentally safe method of controlling low lying vegetation selected from the group consisting of weeds, moss, poison ivy, clover and grass, comprising the steps of:

providing a quantity of sodium bicarbonate adjacent to said low lying vegetation; and applying to the locus thereof sodium bicarbonate in powder form to a thickness in a range of about $\frac{1}{8}$ inch to about $\frac{1}{4}$ inch.

2. The method of claim 1 which said low lying vegetation is wet when said sodium bicarbonate is applied.

3. An environmentally safe method of controlling low lying vegetation selected from the group consisting of weeds, moss, poison ivy, clover and grass, comprising the steps of:

providing a quantity of sodium bicarbonate adjacent to said low lying vegetation; and applying to the locus thereof sodium bicarbonate in liquid form in a concentration of about one part water, by volume, to about one part sodium bicarbonate, by volume.

* * * * *